United States Patent [19]

Picataggio et al.

[11] Patent Number: 5,514,583
[45] Date of Patent: May 7, 1996

[54] RECOMBINANT ZYMOMONAS FOR PENTOSE FERMENTATION

[75] Inventors: Stephen K. Picataggio, Golden; Min Zhang, Lakewood; Christina K. Eddy, Littleton; Kristine A. Deanda, Lakewood; Mark Finkelstein, Fort Collins, all of Colo.

[73] Assignee: Midwest Research Institute, Kansas City, Mo.

[21] Appl. No.: 228,303

[22] Filed: Apr. 15, 1994

[51] Int. Cl.$^6$ .............. C12N 1/21; C12N 15/74; C12N 15/63; C12P 7/06
[52] U.S. Cl. .............. 435/252.3; 435/243; 435/320.1; 435/822; 435/161; 435/163; 435/165; 536/23.7; 536/23.2; 935/29; 935/60; 935/72
[58] Field of Search .................. 435/252.3, 243, 435/320.1, 822, 161, 163, 165; 536/23.7, 23.2; 935/72, 60, 29

[56] References Cited

U.S. PATENT DOCUMENTS

| | | | |
|---|---|---|---|
| 4,731,329 | 3/1988 | Lawford | 435/162 |
| 4,812,410 | 3/1989 | Lawford | 435/161 |
| 4,816,399 | 3/1989 | Lawford | 435/161 |
| 4,876,196 | 10/1989 | Salzbrunn et al. | 435/161 |
| 5,000,000 | 3/1991 | Ingram et al. | 435/161 |
| 5,028,539 | 7/1991 | Ingram et al. | 435/161 |
| 5,041,378 | 8/1991 | Drummond et al. | 435/234 |
| 5,168,056 | 12/1992 | Frost | 435/172.3 |
| 5,266,475 | 11/1993 | Lee et al. | 435/234 |
| 5,272,073 | 12/1993 | Frost et al. | 435/155 |

OTHER PUBLICATIONS

M. Tantirungkij et al. J. Ferment. Bioeng. 75(2) 83–88 (1993).
P. Kotter et al. Appl. Microbiol. Biotechnol. 38:776–783 (1993).
G. A. Sprenger J. Biotechnol. 27:225–237 (1993).
T. Conway et al. J. Bacteriol. 169(12) 56353–5662 (Dec. 1987).
M. Burnett et al. J. Bacteriol. 174(20) 6548–6553 (Oct. 1992).
T. Yura et al. Nuc. Acids. Res. 20(13) 3305–3308 (Jul. 1992).
P. Kotter et al. Curr. Genetics 18:493–500 (1990).
Feldman et al., 1992. Appl. Microbiol.Biotechnol. 38:354–361.
Liu et al., 1988. J. Biotechnol. 7:61–77.

Primary Examiner—Robert A. Wax
Assistant Examiner—Rebecca Prouty
Attorney, Agent, or Firm—Edna M. O'Connor; Ruth Eure

[57] ABSTRACT

The invention relates to microorganisms which normally do not ferment a pentose sugar and which are genetically altered to ferment this pentose to produce ethanol. A representative example is *Zymomonas mobilis* which has been transformed with *E. coli* xylose isomerase, xylulokinase, transaldolase and transketolase genes. Expression of the added genes are under the control of *Zymomonas mobilis* promoters. This newly created microorganism is useful for fermenting pentoses and glucose, produced by hydrolysis of hemicellulose and cellulose, to produce ethanol.

9 Claims, 2 Drawing Sheets

RECOMBINANT ZYMOMONAS FOR PENTOSE FERMENTATION

The United States Government has rights in this invention pursuant to Contract No. DE-AC02-83CH10093 between the United States Department of Energy and the Midwest Research Institute.

FIELD OF THE INVENTION

This invention relates to recombinant *Zymomonas mobilis* strains, metabolizing xylose and bearing xylose utilization and pentose phosphate pathway genes, useful for the fermentation of the xylose component in cellulosic biomass to ethanol. This invention also relates to the process of using these strains for the rapid and efficient fermentation of the xylose component in cellulosic biomass to ethanol.

BACKGROUND OF THE INVENTION

Cellulosic biomass is a favorable feedstock for fuel ethanol production because it is both readily available and less expensive than either corn or sugarcane. However, substantial hurdles must be overcome before a typical cellulosic feedstock can be utilized effectively as a substrate for the fermentative production of ethanol. The typical feedstock is comprised of approximately 35–45% cellulose, 30–40% hemicellulose, 15% lignin and 10% of other components. The cellulose fraction is comprised of polymers of the hexose sugar, glucose. The hemicellulose fraction is comprised mostly of pentose sugars, and substantially of xylose.

Whereas microorganisms are known that can efficiently ferment the glucose component in cellulose, conversion of the xylose in the hemicellulose fraction to ethanol has been difficult and this remains to be one of the economic bottlenecks in a biomass to ethanol conversion scheme. The rapid and efficient utilization of the xylose component in cellulosic biomass is desirable in the development of a commercial process.

*Zymomonas mobilis* is a bacterium that has been utilized as a natural fermentative agent in the production of alcoholic beverages, such as pulque and palm wines produced from plant saps. Comparative performance trials have suggested that Zymomonas may become an important industrial ethanol-producing microorganism because of its 5–10% higher yield and up to 5-fold higher productivity compared to traditional yeast fermentations. Because of its potential value, several processes based on the use of Zymomonas for the production of industrial ethanol from glucose-based feedstocks have been disclosed in U.S. Pat. Nos. 4,731,329, 4,812,410, 4,816,399, and 4,876,196.

While Zymomonas may become an important fuel ethanol-producing microorganism from glucose-based feedstocks, its substrate utilization range is restricted to fermentation of glucose, sucrose and fructose and, as such, it is not naturally suited for fermentation of the xylose component in cellulosic feedstocks. Zymomonas contains the Entner-Douderoff pathway that allows it to ferment glucose very efficiently to ethanol as the sole fermentation product. However, Zymomonas is naturally unable to ferment the xylose in cellulosic biomass because it lacks the essential pentose metabolism pathways. Thus, an opportunity exists to genetically engineer this organism for the fermentation of xylose to ethanol.

Genetic engineering attempts have been made to enhance ethanol production by fermentation by transferring genes from one species to another. For example, see U.S. Pat. Nos. 5,000,000 and 5,028,539. Gene cloning and expression of various enzymes including enzymes for creating a new metabolic pathway are also known. For example see U.S. Pat. Nos. 5,272,073, 5,041,378, 5,168,056 and 5,266,475. However, none of these discoveries has successfully broadened the fermentable substrate range of a microorganism which could not previously ferment xylose to ethanol.

Previous attempts to introduce a xylose catabolic pathway from either Xanthomonas or Klebsiella into Zymomonas have been unsuccessful and the recombinant strains were incapable of growth on xylose as the sole carbon source (Feldmann et al., 1992. Appl. Microbiol. Biotechnol. 38:354–361; Liu et al., 1988. J. Biotechnol. 7: 61–77).

SUMMARY OF THE INVENTION

The present invention successfully introduces a pentose, such as xylose, catabolic pathway into a microorganism, such as Zymomonas, which previously did not have the ability to ferment xylose into ethanol. For the first time, such microorganisms are capable of growing on xylose as a sole carbon source and fermenting xylose directly to ethanol. By introducing the genes encoding xylose isomerase and xylulokinase, xylose can be converted to xylulose-5-P. Then, by introducing two more genes encoding enzymes in the pentose phosphate pathway, transaldolase and transketolase, xylulose-5-P can be further converted to the key intermediates that couple pentose metabolism to the glycolytic Entner-Douderoff pathway, and consequently, permit the microorganism to metabolize xylose to ethanol.

A further aspect of the present invention is a composition of *Zymomonas mobilis* containing the genes encoding xylose isomerase, xylulokinase, transaldolase and transketolase which may be under the control of one or more promoters recognized by *Z. mobilis*, such that these genes are expressed in *Z. mobilis*. The genes confer the ability to grow on and ferment xylose directly to ethanol upon these cells.

In particular, compositions of *Z. mobilis* are provided which contain the xylose isomerase and xylulokinase genes from *Escherichia coli* which may be cloned precisely under the control of the *Z. mobilis* glyceraldehyde-3-phosphate dehydrogenase (GAP) promoter. The transaldolase and transketolase genes from *Escherichia coli* which may be cloned precisely under the control of the *Z. mobilis* enolase (ENO) promoter, are also provided to *Z. mobilis*. All four of these genes are expressed in the cells of *Z. mobilis* conferring upon these cells the ability to grow on and ferment xylose directly to ethanol. The cloned genes may be provided on any number of vectors but preferably are contained on a single plasmid vector. More preferably, the genes are integrated into the host genome.

Another aspect of the present invention is cultures of microorganisms with the above described abilities. The cultures may be biologically pure or be mixed with other strains or different organisms to aid in the metabolism of the substrates or a mixture of substrates into ethanol. A related aspect of the present invention is the culture broth per se which may tolerate a small amount of contamination.

Yet another aspect of the present invention is a process for producing ethanol from a pentose, such as xylose, or cellulosic feedstocks containing hemicellulose, by culturing the above mentioned genetically-engineered microorganisms in a culture medium containing the pentose.

An additional aspect of the present invention is the modification of the catabolic pathway of a microorganism, such as Zymomonas, which previously did not have the ability to ferment arabinose into ethanol. Such microorganisms are capable of growing on arabinose as a sole carbon source and fermenting arabinose directly to ethanol. By introducing the genes converting arabinose into ethanol, a microorganism without arabinose fermentation ability may be converted into a microorganism capable of fermenting arabinose into ethanol.

The introduction of the genes for L-arabinose isomerase, L-ribulokinase, and L-ribulose 5-phosphate 4-epimerase in addition to transaldolase and transketolase should allow a microbe, such as Zymomonas, to metabolize arabinose to ethanol.

DESCRIPTION OF THE PREFERRED EMBODIMENTS

The invention is the development of recombinant Zymomonas and other microbial strains with an expanded substrate utilization range and which are capable of growth on and/or efficient ethanol production from xylose or other pentoses as the sole carbon source.

The microorganisms used to prepare the present invention are those which are capable of being genetically altered to produce the necessary enzymes to form a metabolic pathway for catabolizing pentoses, particularly xylose. The microorganism may naturally have some enzymes in the pathway but will not be able to ferment xylose into ethanol until it has been genetically altered.

The manner of genetic alteration may use any combination of known genetic engineering techniques such as mutation and addition of foreign DNA, provided that the microorganism is able to ferment a pentose to ethanol after treatment. Foreign DNA may be introduced into the microorganism by any conventional technique such as conjugation, transformation, transduction or electroporation.

Many microorganisms which are capable of fermenting sugars to ethanol lack at least one of the genes for the enzymes which make up a metabolic pathway for converting xylose and other pentoses into ethanol. Exogenous genes may be added to complete a metabolic pathway. One need not add genes necessary for every step if the host microorganism already produces an enzyme in the pathway. The number of genes to be added will depend on the starting microorganism. In the situation of naturally occurring *Zymomonas mobilis*, four genes may be added or native genes altered to complete the pathway for metabolizing xylose to an intermediate which is further metabolized to ethanol using the glycolytic Entner-Douderoff pathway.

The indigenous Zymomonas genes may be altered by any known genetic manipulation technique to provide a protein with the necessary enzyme activity to produce the desired metabolic pathway. The altered genes may complement one or more of the introduced genes from another host to complete the metabolic pathway. The use of this procedure may be advantageous by reducing the number of genes one needs to add to the host cell. For example, Zymomonas's native transketolase may be used to substitute for a foreign transketolase gene, such as the one disclosed from *E. coli*.

Sufficient genes may be added so that the recipient microorganism may ferment xylose or other pentose sugars as the sole carbon source. The microorganism may or may not be able to multiply on xylose as the sole carbon source but may be capable of fermenting xylose to ethanol.

A gene may be added to a cell by way of a vector. The vector may be in the form of a plasmid, cosmid or virus which is compatible to the cell's DNA and any resident plasmids. Generally, vectors either integrate into the recipient microorganism's DNA or the vector has an origin of replication to stably maintain the vector throughout many microbial generations. The origin of replication may code for either stringent or non-stringent replication.

To express the gene(s), a structural gene is generally placed downstream from a promotor region on the DNA. The promotor must be recognized by the recipient microorganism. In addition to the promotor, one may include regulatory sequences to either increase expression or to control expression. Expression may be controlled by an inducer or a repressor so that the recipient microorganism expresses the gene(s) only when desired.

In a preferred embodiment of the invention, xylose or other pentose metabolic pathway genes are obtained from a xylose metabolizing microorganisms and added to Zymomonas which does not ferment xylose to ethanol. Especially preferred is *Zymomonas mobilis* which historically has been used for fermenting sugar containing liquids (plant sap) into alcoholic beverages. Certain strains of Zymomonas are tolerant of up to 1.5% sodium chloride and other mutants are tolerant to acetic acid, other microbial inhibitors, high temperatures and/or high ethanol concentrations. The selection of host strain will depend on the substrate being used.

In another embodiment of the invention, the source for the genes encoding xylose metabolism is Xanthomonas, Klebsiella, *E. coli*, Rhodobacter, Flavobacterium, Acetobacter, Gluconobacter, Rhizobium, Agrobacterium, Salmonella, Pseudomonads and Zymomonas. In general the source of the genes for pentose metabolism is any Gram-negative bacterium capable of utilizing pentose sugars for growth. A preferred organism for the source of genes is *E. coli*. The preferred genes encode L-arabinose isomerase, L-ribulokinase, and L-ribulose 5-phosphate 4-epimerase, xylose isomerase, xylulokinase, transaldolase and transketolase. Expression of these genes is under the control of promoters that function in Zymomonas. Strong glycolytic promoters are preferred. The promoters for glyceraldehyde-3-phosphate dehydrogenase and enolase are particularly preferred. Different genes may be under the control of different promoters or other expression altering sequences.

Some or all of the genes may be located together in the same vector or they may be on different vectors or integrated into the genome. Their expression may be so that the newly formed metabolic pathway is formed to enable the microorganism to ferment xylose or other pentoses to ethanol. Preferably, the genes for xylose isomerase, xylulokinase, transaldolase and transketolase are under the control of one or more functional promoters when in Zymomonas. The genes on a vector may be in any order, grouping or orientation relative to each other, providing that, if more than one promotor is present on the vector, the direction of transcription from one promotor does not adversely affect expression of the genes.

In other preferred embodiments of the present invention, a genetic element comprising any two or more of the above described genes may be placed on the same vector. Particularly preferred is a plasmid containing both the transaldolase and the transketolase genes. These vectors preferably have the genes under the control of a promotor recognized by Zymomonas. The Examples below show pZBET, pZB4 and pZB5, all of which are examples of vectors carrying DNA encoding two or more of the above described genes.

The expression of the four genes and the resulting functional activity of their corresponding gene products represent a new biochemical pathway that links xylose metabolism to the central Entner-Douderoff pathway in Zymomonas, conferring upon these cells, for the first time, the ability to grow on and ferment xylose directly to ethanol. The genes on a vector may be in any orientation relative to the direction of transcription of these genes provided that they do not interfere with each other. The examples below have shown the genes to perform in essentially the same way regardless of the orientation.

The microorganism according to the present invention may be mixed with any xylose or other pentose containing medium and allowed to ferment the medium to produce ethanol. The medium may include other fermentable sugars, such as glucose. If microbial growth is desired, other nutrients which are necessary for microbial growth may be added and the microorganism allowed to reproduce.

Transaldolase and transketolase are key enzymes of the pentose phosphate pathway and are required for fermentation of any pentose sugar by Zymomonas to ethanol. Another preferred embodiment is the expression of these genes in Zymomonas in conjunction with any other set of genes that allow the utilization of a specific pentose sugar, such as xylose or arabinose. An example of added genes needed for fermentation of arabinose are L-arabinose isomerase, L-ribulokinase, and L-ribulose 5-phosphate 4-epimerase genes in addition to transaldolase and transketolase genes.

In an especially preferred embodiment of the invention, xylose, arabinose and other pentose utilization genes along with the genes for transaldolase and transketolase are obtained from organisms that contain these genes and are expressed in Zymomonas. Efficient transport of the pentoses into Zymomonas may be through native Zymomonas transport proteins, mutated Zymomonas transport proteins, or through the addition of new facilitated transporters introduced by cloning new transport genes into Zymomonas with or without mutagenesis of the cloned transport genes.

The step of microbial growth may be separate from fermentation. Xylose and other pentoses may be used as a carbon source for microbial growth or one can separately culture the microorganism on any medium (with or without a pentose) until sufficient numbers of microorganisms are present as a first step and then a xylose containing medium is added for fermentation in a second step. If a two step method is used, one may control expression of the genes in the new metabolic pathway so that greater expression occurs during the second step.

The choice of substrates will depend on cost and supply of the substrate to be fermented to ethanol. A typical low-cost supply of pentoses is from hemicellulose. Xylose and other pentoses are liberated from hemicellulosic materials by steam and/or an acid or alkali. Smaller amounts of other sugars such as glucose are also separated during this treatment and are also fermented by Zymomonas to ethanol.

When the substrate is cellulosic materials, the cellulose may be hydrolyzed to sugars simultaneously or separately and also fermented to ethanol. Since hemicellulose is generally easier to hydrolyze to sugars than cellulose, it is preferable to first prehydrolyze the cellulosic material, separate the pentoses and then hydrolyze the cellulose by treatment with steam and/or acid or alkali or cellulases to form glucose. Both sugars may be simultaneously or separately fermented to ethanol using the microorganism of the present invention. If so desired, the hexoses may be fermented by a different microorganism to ethanol, such as yeast, natural Zymomonas, etc.

Many fermentation conditions are known per se as shown by the patents mentioned in the Background of the Invention section above. *Zymomonas mobilis* is a facultative anaerobic bacterium. It has theoretical yields of ethanol from sugar of up to 97% which provides for little microbial growth if so desired. The pH conditions are 3.5 to 7.5. Substrate concentrations of up to 25% (based on glucose), and under some conditions even higher, may be used. Unlike other ethanol producing microorganisms, no oxygen is needed at any stage for microorganism survival. Also unlike yeast, oxygen does not drastically reduce ethanol productivity or greatly increase cell growth. Agitation is not necessary but may be desirable to enhance availability of substrate and diffusion of ethanol. Accordingly, the range of fermentation conditions may be quite broad. Likewise, any of the many known types of apparatus may be used for the present invention.

The microorganism according to the present invention may be used as a biologically pure culture or it may be used with other ethanol producing microorganisms in mixed culture. Biologically pure cultures are generally easier to optimize but mixed cultures may be able to utilize additional substrates. One may also add enzyme(s) to the fermenter to aid in the degradation of substrates or to enhance ethanol production. For example, cellulase may be added to degrade cellulose to glucose simultaneous to the fermentation of glucose to ethanol. Likewise, a hemicellulase may be added to degrade hemicellulose.

In the preferred embodiment using a genetically engineered Zymomonas, Zymomonas cultures are relatively resistant to contamination by other microorganisms. Nonetheless, it is preferred to sterilize or at least kill substantially all microorganisms in the substrate being added to the Zymomonas culture.

After fermentation, the ethanol, which may achieve concentrations of up to about 13%, is separated from the fermentation broth by any of the many conventional techniques known to separate ethanol from aqueous solutions. These methods include evaporation, distillation, solvent extraction and membrane separation. Particles of substrate or microorganism may be removed before ethanol separation to enhance separation efficiency.

Once the fermentation is complete, excess microorganism and unfermented substrate may be either recycled or removed in whole or in part. If removed, the microorganism may be killed, dried or otherwise treated. This mixture may be used as animal feed, fertilizer, burnt as fuel or discarded.

While the discussion of the fermentation in this specification generally refers to a batch process, parts or all of the entire process may be performed continuously. To retain the microorganism in the fermenter, one may separate solid particles from the fluids. This may be performed by centrifugation, flocculation, sedimentation, filtration, etc. Alternatively, the microorganism may be immobilized to retain it in the fermenter or to provide easier separation.

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are better illustrated by the use of the following non-limiting examples.

EXAMPLE 1

Isolation of the Xylose Isomerase and Xylulokinase Genes and Fusion to a Zymomonas GAP Promoter The *Escherichia coli* xylose isomerase and xylulokinase genes were initially obtained on a 7 kb HpaI/EcoRI restriction fragment from plasmid pLC1-3 (Clarke, L. and J. Carbon, 1977. Cell. 9:91–99). This DNA fragment was recovered from an agarose gel and subcloned into the SmaI/EcoRI sites in a pBlueScript plasmid (Strategene, LaJolla, Calif.), which had been dephosphorylated with calf intestinal phosphatase, to generate the plasmid designated pBSX.

To remove excess DNA, pBSX was digested either with NsiI and HindIII or with NsiI and SmaI. After treatment with T4 DNA polymerase, the digested DNAs were separately ligated under dilute conditions favoring intramolecular ligation and were then transformed into *E. coli* HB101. Restriction analyses of the plasmid DNA from ampicillin-resistant transformants confirmed the presence of the expected deletion derivatives. The plasmid with the expected 587 bp NsiI/HindIII deletion was designated pXKH and contains the xylose isomerase and xylulokinase genes with the 3'-flanking xylose operon transcriptional terminator. The plasmid with the approximately 900 bp NsiI/SmaI deletion was designated pXKS and contains the xylose isomerase and xylulokinase genes without the 3'-flanking xylose operon transcriptional terminator.

To express the xylose isomerase and xylulokinase genes in Zymomonas, they were precisely fused to a Zymomonas glyceraldehyde-3-phosphate dehydrogenase (GAP) promoter using a polymerase chain reaction (PCR)-mediated overlap extension technique. This approach allowed precise fusion of the GAP promoter containing a ribosome binding site to the translational start codon of the xylose isomerase gene, thus ensuring that the expression of the xylose isomerase and xylulokinase genes would be regulated solely by the GAP promoter.

To accomplish this precise fusion, 308 bp of 5'-flanking DNA upstream of the GAP structural gene comprising the GAP promoter and the first 893 bp of the xylose isomerase structural gene were separately synthesized in a PCR using a common linking oligonucleotide primer. The individual DNA fragments were recovered from an agarose gel and combined in a second PCR in which the complementary ends at the 3'-end of the GAP promoter and the 5'-end of the xylose isomerase gene were annealed. The addition of the 5'-GAP and 3'-xylA primers then allowed the synthesis of a 1213 bp DNA fragment comprising a precise fusion of the GAP promoter to the 5'-end of the xylose isomerase gene.

The primers used to synthesize the 308 bp DNA fragment comprising the GAP promoter were based on the known DNA sequence of the 5'-flanking region of the GAP gene (Conway et al., 1987. J. Bacteriol. 169: 5653–5662) and included:

```
                     NotI
5'-PRIMER:  5'- CCCTCGAGCGGCCGCGTTCGATCAACAACCCGAATCCTATCG-3',SEQ ID NO: 1
                XhoI

3'-PRIMER:  5'-GGTCAAAATAGGCTTGCATGTTTATTCTCCTAACTTATTAAGTAGCTATTATATTCC-3',SEQ ID NO: 2
```

A 15 bp DNA sequence, comprising restriction sites for the restriction enzymes XhoI and NotI, was incorporated at the 5'-end of the synthesized GAP promoter. A 19 bp DNA sequence (BOLD), corresponding to the 5'-end of the xylose isomerase structural gene, was added to the 3'-end of the synthesized GAP promoter.

The primers used to synthesize the DNA fragment comprising the first 893 bp of the xylose isomerase structural gene were based on its known DNA sequence (Lawlis et al., 1984, Appl. Environ. Microbiol. 47: 15–21) and included:

```
5'-PRIMER:  5'-GTTAGGAGAATAAACATGCAAGCCTATTTTGACCAGCTCGATCGCG-3',SEQ ID NO: 3

5'-GGTTGGCGTCGACAGAAC-3',SEQ ID NO: 4
        SalI
```

An 18 bp DNA sequence (BOLD), corresponding to the 3'-end of the GAP promoter was added to the 5'-end of the synthesized xylose isomerase structural gene fragment.

Figure 1:
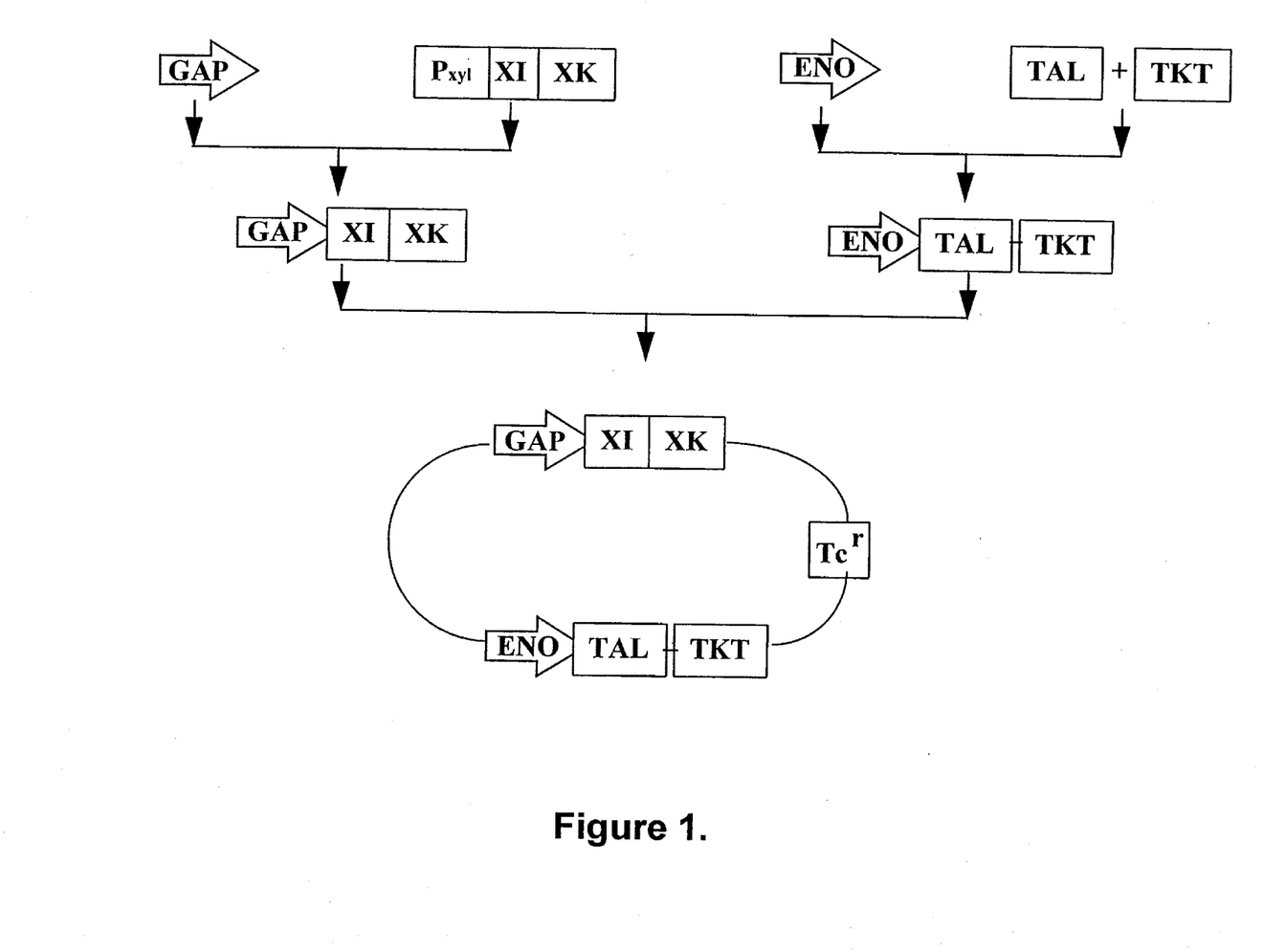
FIG. 1 shows a schematic of a process for producing a recombinant plasmid.

The 1213 bp DNA fragment, comprising a precise fusion of the GAP promoter to the 5'-end of the xylose isomerase gene was used to replace a 2.5 kb XhoI/SalI restriction fragment containing the native xylose isomerase promoter and 5'-end of the xylose isomerase gene in plasmids pXKH and pXKS. The 1213 bp DNA fragment was digested with SalI and XhoI restriction endonucleases and ligated separately to the larger of the two SalI/XhoI restriction fragments from plasmids pXKH and pXKS, previously purified by preparative agarose gel electrophoresis. The ligated DNA was used to transform *E. coli* HB101 and restriction analyses of the plasmid DNA from ampicillin-resistant transformants confirmed the presence of the expected plasmids, which have been designated as pGapXKH and pGapXKS. Digestion of either plasmid with the NotI restriction enzyme liberates the approximately 4.1 kb and 4.4 kb restriction fragments, respectively, containing the xylose isomerase and xylulokinase genes under the control of the GAP promoter, hereafter referred to as the GAP-xylA/xylB operon. This construct is shown in FIG. 1.

EXAMPLE 2

Isolation and Linkage of the Transaldolase and Transketolase Genes in a Synthetic Operon Under Control of a Zymomonas ENO Promoter The *Escherichia coli* transaldolase and transketolase genes were isolated separately, synthetically linked and precisely fused to the Zymomonas enolase (ENO) promoter by PCR-mediated overlap extension. The transaldolase gene, localized within 0'–2.5' minutes of the *Escherichia coli* genome, was obtained by PCR synthesis from total genomic DNA. The primers used to synesize the 954 bp DNA fragment comprising the transaldolase gene were based on its known DNA sequence (Yura et al., 1992. Nucleic Acids Res. 20: 3305–3308) and included:

5'-PRIMER: 5'-CGTCTAAAAGATTTTAAGAAAGGTTTCGATATGACGGACAAATTGACC-3'

3'-PREIMER: 5'CATTTTGACTACC<u>AGATCT</u>AGATTACAGCAGATCGCCGATCATTTTTTCC-3',SEQ ID NO: 7
           XbaI A 33 bp DNA sequence (BOLD), corresponding to the 3'-end of the ENO promoter was added to the 5'-end of the synthesized transaldolase gene. A 21 bp DNA sequence comprising a restriction site for the restriction enzyme XbaI was incorporated at the 3'-end of the synthesized transaldolase gene to facilitate its subsequent subcloning.

The primers used to synthesize the 196 bp DNA fragment comprising the ENO promoter were based on the known DNA sequence of the 5'-flanking region of the ENO gene (Burnett et al., 1992. J. Bacteriol. 174: 6548–6553) and included:

5'-PRIMER: 5'-CC<u>AGATCT</u>CCAGTTACTCAATACG-3',SEQ ID NO: 7
     <u>BglII</u>

3'-PRIMER: 5'-GGTCAATTTGTCCGTCATATCGAAACCTTTCTTAAAATCTTTTAGACG-3',SEQ ID NO: 8

A 6 bp DNA sequence comprising a restriction site for the restriction enzyme BglII was incorporated at the 5'-end of the synthesized ENO promoter to facilitate its subsequent subcloning. An 18 bp DNA sequence (BOLD), corresponding to the 5'-end of the transaldolase gene was added to the 3'-end of the synthesized ENO promoter.

The transaldolase gene (tal) was then precisely fused to the ENO promoter by PCR-mediated overlap extension. To accomplish this precise fusion, the 196 bp of 5'-flanking DNA upstream of the ENO structural gene comprising the ENO promoter and the 954 bp DNA fragment comprising the transaldolase gene were separately synthesized in a PCR using a common linking oligonucleotide primer. The individual DNA fragments were recovered from an agarose gel and then combined in a second PCR in which the complementary ends at the 3'-end of the ENO promoter and the 5'-end of the transaldolase gene were annealed. The addition of the 5'-ENO and the 3'-tal primers then allowed the synthesis of a 1174 bp DNA fragment comprising a precise fusion of the ENO promoter to the transaldolase gene. This 1174 bp DNA fragment was digested with the XbaI restriction enzyme and then ligated to plasmid pUC18 that had been sequentially digested with the SmaI restriction enzyme, treated with Taq polymerase in the presence of dTTP and finally digested with XbaI. The ligated DNA was used to transform *E. coli* DH5α and restriction analyses of the plasmid DNA from ampicillin-resistant transformants confirmed the presence of the expected plasmid, which has been designated as pEnoTAL.

The transketolase gene (tktA) was obtained by PCR synthesis from *E. coli* W3110 genomic DNA. The primers used to synthesize the 2077 bp DNA fragment comprising the transketolase gene were based on its known DNA sequence. (Sprenger, 1992. J. Bacteriol. 174: 1707–1708) and included:

5'-PRIMER: 5'-GC<u>TCTAGA</u>CGATCTGGAGTCAAAATGTCC-3',SEQ ID NO: 9
    <u>XbaI</u>

3',SEQ ID NO: 10-PRIMER: 5'-AGATCTGCGCAAACGGACATTATCAAGG-3'
           BglII A 8 bp DNA sequence comprising a restriction site for the restriction enzyme XbaI was incorporated at the 5'-end of the tktA gene and a 7 bp DNA sequence comprising a restriction site for the restriction enzyme BglII was incorporated at the 3'-end of the tktA gene to facilitate its subsequent subcloning. Following PCR synthesis, the 2077 bp DNA fragment comprising the transketolase gene was purified by preparative agarose gel electrophoresis, digested with the XbaI restriction enzyme and ligated to plasmid pUC18 that had been sequentially digested with the HincII restriction enzyme, treated with Taq polymerase in the presence of dTTP and finally digested with XbaI. The ligated DNA was used to transform *E. coli* DH5α and restriction analyses of the plasmid DNA from ampicillin-resistant transformants confirmed the presence of the expected plasmid, which has been designated as pUC-TKT.

The transketolase gene was then subcloned downstream of the ENO-transaldolase fusion to create a synthetic operon comprised of the transaldolase and transketolase genes both under the control of the ENO promoter. To do this, plasmid pUC-TKT was digested with the XbaI and SphI restriction enzymes and the approximately 2 kb restriction fragment containing the transketolase gene was purified by preparative agarose gel electrophoresis and ligated to plasmid pEno-TAL that had been previously digested with the same restriction enzymes. The ligated DNA was used to transform *E. coli* DH5α and restriction analyses of the plasmid DNA from ampicillin-resistant transformants confirmed the presence of the expected plasmid, which has been designated as pEnoTAL/TKT. Digestion of this plasmid with the BglII restriction enzyme liberates an approximately 3 kb restriction fragment containing the transaldolase and transketolase operon under the control of the ENO promoter, hereafter referred to as the ENO-tal/tkt operon. This construct is also shown in FIG. 1.

EXAMPLE 3

Construction of a Shuttle Vector and Transfer of the Xylose Metabolism and Pentose Phosphate Pathway Genes into Zymomonas A shuttle vector was constructed to permit the simultaneous transfer of the xylose metabolism and pentose phosphate pathway genes into Zymomonas. A small native 2.7 kb plasmid from *Z. mobilis* ATCC 10988 was purified by preparative agarose gel electrophoresis, linearized by digestion with the AvaI restriction enzyme and ligated to the similarly digested plasmid pACYC184 (New England BioLabs, Beverly, Mass.) which had been dephosphorylated by treatment with calf intestinal phosphatase. The ligated DNA was used to transform *E. coli* HB101 and restriction analyses of the plasmid DNA from tetracycline-resistant transformants confirmed the presence of the expected plasmid, which has been designated as pZB186.

This plasmid was then modified to accept the xylose metabolism genes on a single NotI restriction fragment. Plasmid pZB186 was linearized with the EcoRI restriction enzyme and the cohesive ends were filled-in by treatment with the Klenow fragment of DNA polymerase. NotI linkers were added according to standard methodology and then the plasmid was digested with the NotI restriction enzyme and ligated under dilute conditions favoring intramolecular ligation. The ligated DNA was used to transform *E. coli* DH5α and restriction analyses of the plasmid DNA from tetracycline-resistant transformants confirmed the presence of the added NotI restriction site in pZB186. The modified plasmid has been designated pZB188.

To introduce the ENO-tal/tkt operon into this shuttle vector, the approximately 3 kb BglII restriction fragment from plasmid pEnoTAL/TKT was purified by preparative agarose gel electrophoresis and ligated to pZB188 that had been sequentially passaged through *E. coli* JM110, linearized by digestion with the BclI restriction enzyme and dephosphorylated by treatment with calf intestinal phosphatase. The ligated DNA was used to transform *E. coli* DH5α and restriction analyses of the plasmid DNA from tetracycline-resistant transformants confirmed the presence of the expected plasmid, which has been designated as pZBET.

To also introduce the GAP-xylA/xylB operon into this plasmid, the approximately 4.1 kb and 4.4 kb NotI restriction fragments from plasmids pGapXKH and pGapXKS, respectively, were purified by preparative agarose gel electrophoresis and separately ligated to NotI linearized pZBET. The ligated DNA was used to transform *E. coli* HB101 and restriction analyses of the plasmid DNA from tetracycline-resistant transformants confirmed the presence of the expected plasmids. The plasmid containing the GAP-xylA/xylB operon from pGapXKH in clockwise orientation and the ENO-tal/tkt operon from pEnoTAL/TKT in counterclockwise orientation has been designated pZB4. The plasmid containing the GAP-xylA/xylB operon from pGapXKS in clockwise orientation and the ENO-tal/tkt operon from pEnoTAL/TKT in counterclockwise orientation has been designated pZB5. The orientation of pZB4 and pZB5 may be viewed in FIG. 1.

Plasmids pZB4 and pZB5 were separately transformed into *Z. mobilis* CP4 by electroporation of approximately $10^9$ cells/ml with 4 µg DNA in 40 µl of 10% (w/v) glycerol at 16 kv/cm, 200Ω and 25 µF. After electroporation, the cells were allowed to recover at 30° C. for 3–16 hours in a liquid medium comprised of 5% glucose, 10% yeast extract (Difco), 5% Tryptone (Difco), 0.25% ammonium sulfate, 0.02% potassium phosphate, dibasic and 1 mM magnesium sulfate. Transformants containing pZB4 and pZB5 were isolated following anaerobic incubation at 30° C. for 2 or more days in the same medium additionally containing 1.5% agar and tetracycline (20 µg/ml) and were subsequently confirmed by restriction analyses of the plasmid DNA from tetracycline-resistant transformants.

Enzymatic analyses of *Z. mobilis* CP4 (pZB4) demonstrated the presence of xylose isomerase (0.35 U/min/mg), xylulokinase (1.4 U/min/mg), transaldolase (1.9 U/min/mg) and transketolase (0.27 U/min/mg) activities and thus confirmed the expression of all four genes. These enzymatic activities were either undetectable or significantly lower (xylose isomerase, 0.008/min/mg; xylulokinase, undetectable; transaldolase, 0.014 U/min/mg; and transketolase, 0.032 U/min/mg) in the control strain containing the shuttle vector alone (CP4 [pZB186]).

EXAMPLE 4

Fermentation Performance of Recombinant Zymomonas Containing the Xylose Metabolism and Pentose Phosphate Pathway Genes The fermentation performance of the recombinant Zymomonas containing the xylose isomerase, xylulokinase, transaldolase and transketolase genes was evaluated in a medium comprised of 1% (w/v) yeast extract (Difco), 0.2% potassium phosphate, dibasic and either 5% glucose, or 5% xylose, or 2.5% glucose and 2.5% xylose.

The recombinant Zymomonas strains were first propagated at 30° C. in the above medium containing 5% glucose or xylose in a bottle with 80 ml of working volume without agitation until late log-phase. The cells were then inoculated to 200 ml of the above fermentation medium in a 250 ml flask at an initial $OD_{600}=0.05$–0.1. The cultures were grown at 30° C. under anaerobic conditions using $CO_2$-traps with gentle shaking (150 rpm) for mixing. The cell growth was monitored as optical density at 600 nm. The residual sugars as well as ethanol concentrations were determined on HPLC (HP 1090L) (Hewlett Packard, Wilmington, Del.) using a Bio-Rad Aminex HPX-97H column.

Figure 2:
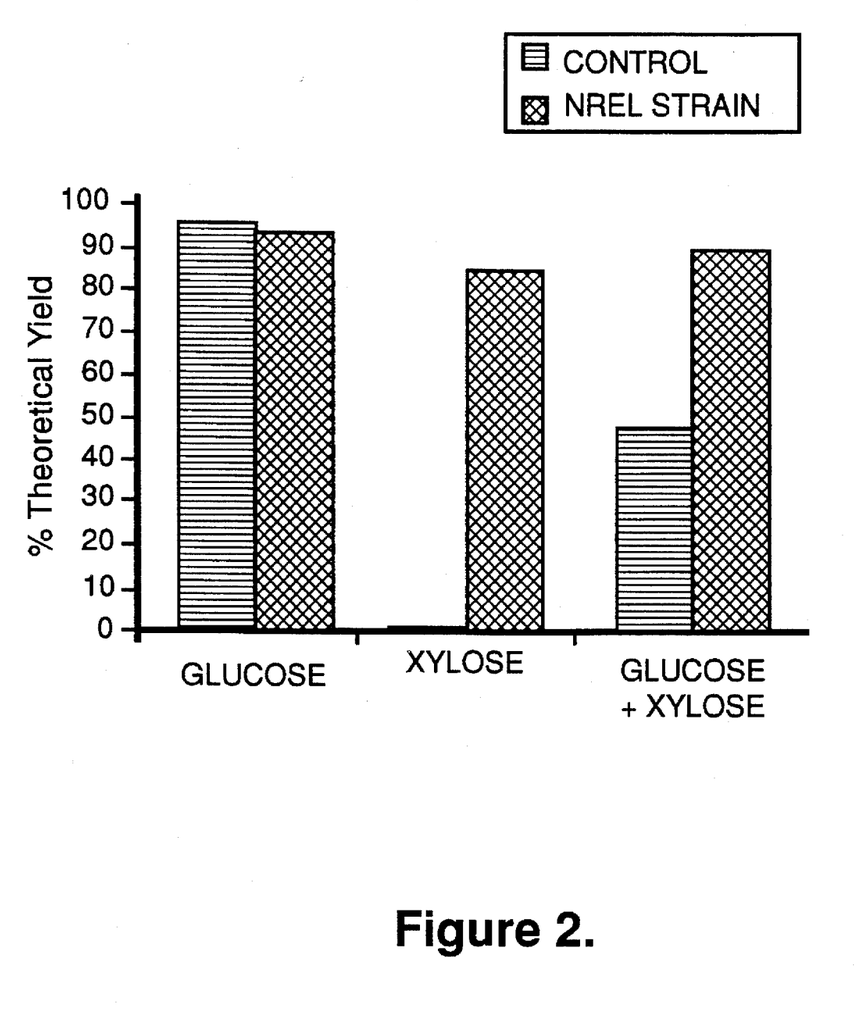
FIG. 2 shows the yield of ethanol using a control *Zymomonas mobilis* and the present recombinant strain when grown on certain sugars or a mixture of certain sugars as the carbon source.

The results presented in FIG. 2 show that in contrast to the control strain containing the shuttle vector alone (CP4 [pZB186]), the recombinant containing the added xylose isomerase, xylulokinase, transaldolase and transketolase genes demonstrated growth on and ethanol production from xylose as a carbon source. The recombinant strain produces ethanol from glucose as efficiently as the control strain at 94% of theoretical yield. The recombinant strain additionally produces ethanol from xylose at 84% of theoretical yield in 79 hours. Furthermore, in the combined presence of glucose and xylose, the recombinant strain ferments both sugars simultaneously to ethanol at 88% of theoretical yield within 48 hours, thus providing the foundation for advanced process designs with cofermentation of mixed-sugar feedstocks.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references mentioned in this application are incorporated by reference.

What is claimed is:
1. A microorganism of the genus Zymomonas containing exogenous genes encoding xylose isomerase, xylulokinase, transaldolase and transketolase and further comprising at least one promotor recognized by Zymomonas which regulates the expression of at least one of said genes, and wherein said microorganism is capable of growing on xylose as a sole carbon source and fermenting said xylose to ethanol at about 88% theoretical yield and, wherein said microorgan- ism without said genes is incapable of growing on or fermenting said xylose to ethanol.

2. A microorganism according to claim 1, wherein the genes encoding xylose isomerase, xylulokinase, transaldolase and transketolase were obtained from bacteria selected from the group consisting of Xanthomonas, Klebsiella, *E. coli*, Rhodobacter, Flavobacterium, Acetobacter, Gluconobacter, Rhizobium, Agrobacterium, Salmonella and Pseudomonads.

3. A microorganism according to claim 1, wherein the genes are integrated into the host genome.

4. A microorganism according to claim 1, wherein said genes are contained on a vector.

5. A microorganism according to claim 4, wherein said xylose isomerase and xylulokinase genes are expressed under the control of a glyceraldehyde-3-phosphate dehydrogenase promoter recognized by Zymomonas and said transaldolase and transketolase genes are expressed under the control of a enolase promoter recognized by Zymomonas.

6. A vector comprising genes encoding xylose isomerase, xylulokinase, transaldolase and transketolase and at least one promoter recognized by Zymomonas which regulates expression of said genes.

7. A vector according to claim 6, wherein the enzymes transaldolase and transketolase are regulated by an enolase promoter recognized by Zymomonas.

8. A vector according to claim 6, wherein the genes encoding xylose isomerase and xylulokinase are regulated by a glyceraldehyde-3-phosphate, dehydrogenase promoter recognized by Zymomonas.

9. A microorganism according to claim 2, wherein the genes encoding xylose isomerase, xylulokinase, transaldolase and transketolase are obtained from *E. coli*.

\* \* \* \* \*

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( v ) FRAGMENT TYPE: internal

( x i ) SEQUENCE DESCRIPTION: SEQ ID NO:1:

CCCTCGAGCG GCCGCGTTCG ATCAACAACC CGAATCCTAT CG    42

( 2 ) INFORMATION FOR SEQ ID NO:2:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( v ) FRAGMENT TYPE: internal

( x i ) SEQUENCE DESCRIPTION: SEQ ID NO:2:

GGTCAAAATA GGCTTGCATG TTTATTCTCC TAACTTATTA AGTAGCTATT ATATTCC    57

( 2 ) INFORMATION FOR SEQ ID NO:3:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO (v) FRAGMENT TYPE: internal (xi) SEQUENCE DESCRIPTION: SEQ ID NO:3:

GTTAGGAGAA TAAACATGCA AGCCTATTTT GACCAGCTCG ATCGCG   46

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(v) FRAGMENT TYPE: internal

(xi) SEQUENCE DESCRIPTION: SEQ ID NO:4:

GGTTGGCGTC GACAGAAC   18

(2) INFORMATION FOR SEQ ID NO:5:

(i) SEQUENCE CHARACTERISTICS:
        (A) LENGTH: 48 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(v) FRAGMENT TYPE: internal

(xi) SEQUENCE DESCRIPTION: SEQ ID NO:5:

CGTCTAAAAG ATTTTAAGAA AGGTTTCGAT ATGACGGACA AATTGACC   48

(2) INFORMATION FOR SEQ ID NO:6:

(i) SEQUENCE CHARACTERISTICS:
        (A) LENGTH: 49 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO

(iv) ANTI-SENSE: NO

(v) FRAGMENT TYPE: internal

(xi) SEQUENCE DESCRIPTION: SEQ ID NO:6:

CATTTTGACT CCAGATCTAG ATTACAGCAG ATCGCCGATC ATTTTTTCC   49

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (ii) MOLECULE TYPE: DNA (genomic)

(iii) HYPOTHETICAL: NO (iv) ANTI-SENSE: NO (v) FRAGMENT TYPE: internal (xi) SEQUENCE DESCRIPTION: SEQ ID NO:7:

CCAGATCTCC AGTTACTCAA TACG 24

(2) INFORMATION FOR SEQ ID NO:8:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (v) FRAGMENT TYPE: internal (xi) SEQUENCE DESCRIPTION: SEQ ID NO:8:

GGTCAATTTG TCCGTCATAT CGAAATTTTC TTAAAATCTT TTAGACG 47

(2) INFORMATION FOR SEQ ID NO:9:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (v) FRAGMENT TYPE: internal (xi) SEQUENCE DESCRIPTION: SEQ ID NO:9:

GCTCTAGACG ATCTGGAGTC AAAATGTCC 29

(2) INFORMATION FOR SEQ ID NO:10:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (v) FRAGMENT TYPE: internal (xi) SEQUENCE DESCRIPTION: SEQ ID NO:10:

AGATCTGCGC AAACGGACAT TATCAAGG 28